United States Patent
Ochs et al.

(10) Patent No.: US 11,145,420 B2
(45) Date of Patent: *Oct. 12, 2021

(54) RISK MANAGEMENT ON THE APPLICATION OF CROP INPUTS

(75) Inventors: Yanhong Ochs, Waterloo, IA (US); Shawn James McComb, Algonquin, IL (US)

(73) Assignee: FMH Ag Risk Insurance Company, West Des Moines, IA (US)

(*) Notice: Subject to any disclaimer, the term of this patent is extended or adjusted under 35 U.S.C. 154(b) by 1556 days.

This patent is subject to a terminal disclaimer.

(21) Appl. No.: 10/970,624

(22) Filed: Oct. 21, 2004

(65) Prior Publication Data

US 2006/0015253 A1    Jan. 19, 2006

Related U.S. Application Data

(60) Provisional application No. 60/588,808, filed on Jul. 16, 2004.

(51) Int. Cl.
G06Q 40/08    (2012.01)
G16H 80/00    (2018.01)

(52) U.S. Cl.
CPC ............. *G16H 80/00* (2018.01); *G06Q 40/08* (2013.01)

(58) Field of Classification Search
USPC .......................................... 705/4; 701/1, 50
See application file for complete search history.

(56) References Cited

U.S. PATENT DOCUMENTS

| | | | |
|---|---|---|---|
| 4,766,539 A | 8/1988 | Fox | |
| 5,884,224 A * | 3/1999 | McNabb et al. | 702/2 |
| 5,897,614 A | 4/1999 | McKiel, Jr. | 704/208 |
| 5,995,894 A * | 11/1999 | Wendte | 701/50 |
| 6,745,127 B2 | 6/2004 | Crosby | 702/2 |
| 6,745,128 B2 | 6/2004 | Hanson | 702/2 |
| 6,751,515 B2 | 6/2004 | Moore | 700/110 |
| 6,990,459 B2 * | 1/2006 | Schneider | 705/8 |
| 7,039,592 B1 * | 5/2006 | Yegge et al. | 705/4 |
| 2001/0011437 A1 * | 8/2001 | Shortridge et al. | 47/58.1 |
| 2002/0091458 A1 * | 7/2002 | Moore | 700/110 |

(Continued)

OTHER PUBLICATIONS

F.C. Wong; "Economic value of remote sensing imagery for agricultural applications"; 2003 IEEE Aerospace Conference Proceedings (Cat. No. 03TH8652) (vol. 8, pp. 8_3815-8_3829).*

(Continued)

*Primary Examiner* — Gregory A Pollock
(74) *Attorney, Agent, or Firm* — Richard Blakely Glasgow

(57) ABSTRACT

A system and method for managing a crop insurance program facilitates determining an input management plan for application of a crop input to a field within a defined geographic area. A field yield is measured. The field yield pertains to a yield of particular crop associated with a field in a defined geographic area. An aggregate yield is estimated. The aggregate yield relates to the particular crop associated with the defined geographic area. The aggregate yield is scaled to represent a generally equivalent land area to the field. A difference or variation is determined between the field yield and the aggregate yield. The determined difference or indication thereof is made available to a receiving entity (e.g., insurer that is associated with at least one of claims and insurance on the crop in the field).

30 Claims, 10 Drawing Sheets

(56) References Cited

U.S. PATENT DOCUMENTS

| | | | |
|---|---|---|---|
| 2002/0103688 A1 | 8/2002 | Schneider | |
| 2002/0133309 A1* | 9/2002 | Hardt | 702/129 |
| 2002/0173980 A1* | 11/2002 | Daggett et al. | 705/1 |
| 2003/0061075 A1* | 3/2003 | Heckman et al. | 705/4 |
| 2004/0059737 A1* | 3/2004 | Beck et al. | 707/100 |
| 2004/0177326 A1 | 9/2004 | Bibko et al. | |
| 2005/0027572 A1* | 2/2005 | Goshert | 705/4 |
| 2005/0043975 A1 | 2/2005 | Johnson | |
| 2005/0125260 A1* | 6/2005 | Green et al. | 705/4 |

OTHER PUBLICATIONS

Nutrient BMP Endorsement for CRC Policy (online), retrieved on Jun. 6, 2003. Retrieved from the Internet: http://www.rma.usda.gov/FTP/Policies/2003/n-bmp/pdf/CRC_BMP_Endorsement.pdf.

Nutrient BMP Endorsement for MPCI Policy (online), retrieved on Jun. 6, 2003. Retrieved from the Internet: http://www.rma.usda.gov/FTP/Policies/2003/n-bmp/pdf/MPCI_BMP_Endorsement.pdf.

Nutrient BMP Endorsement Underwriting Guide (online), retrieved on Jun. 6, 2003. Retrieved from the Internet: http://www.rma.usda.gov/FTP/Policies/2003/n-bmp/pdf/N-BMP_ur.pdf.

Nutrient Best Management Practice (N-BMP) Handbook (online), retrieved on Jun. 6, 2003. Retrieved from the Internet: http://www.rma.usda.gov/FTP/Publications/directives/20000/pdf/03_20040_BMP_Handbook.pdf.

Nutrient Best Management Practice (N-BMP) Loss Adjustment Handbook (online), retrieved on Jun. 6, 2003. Retrieved from the Internet: http://www.rma.usda.gov/FTP/Publications/directives/20000/pdf/03_20050_BMP_LAH.pdf.

Nutrient BMP Endorsement Premium Calculation Worksheet (online), retrieved on Jun.6, 2003. Retrieved from the Internet: http://www.rma.usda.gov/FTP/Policies/2003/n-bmp/pdf/N-BMP_prem_wksht.pdf.

Nutrient BMP Endorsement Common Questions and Answers (online), retrieved on Jun. 6, 2003. Retrieved from the Internet: http://www.rma.usda.gov/FTP/Policies/2003/n-bmp/pdf/N-BMP_qa.pdf.

U.S. Appl. No. 10/970,241, filed Oct. 21, 2004.

U.S. Appl. No. 10/970,639, filed Oct. 21, 2004.

Cornell University. Adapt-N Increased Grower Profits and Decreased Nitrogen Inputs in 2012 Strip Trials [online] 2012. http://blogs.cornell.edu/whatscroppingup/2013/05/15/adapt-n-increased-grower-profits-and-decreased-nitrogen-inputs-in-2012-strip-trials/ [Retrieved on Aug. 16, 2013].

Rothamsted Research. Soil Sensors for Nitrogen Availability. Department for Environment, Food and Rural Affairs, pp. 1-17, 2005, Harpenden AL5 2JQ, United Kingdom.

* cited by examiner

US 11,145,420 B2

RISK MANAGEMENT ON THE APPLICATION OF CROP INPUTS

This document claims priority based on U.S. provisional application Ser. No. 60/588,808, filed Jul. 16, 2004, and entitled RISK MANAGEMENT ON THE APPLICATION OF CROP INPUTS, under 35 U.S.C. 119(e).

FIELD OF THE INVENTION

This invention relates to the risk management on the application of crop inputs.

BACKGROUND OF THE INVENTION

The identity, timing and amount of application of crop inputs to a field may be determined by one or more of the following factors: maximizing yield of a crop, reducing the overall cost of a crop inputs, varying the rate of application of crop inputs to reduce the cost of crop inputs or to improve yield, complying with governmental regulations, following environmental best practices or voluntary environmental stewardship practices, applying scientific or agronomic models, complying with contractual constraints imposed by purchaser or potential purchasers of a crop, and complying with crop insurance requirements or crop insurance endorsements. For example, a scientific or computer model may be applied to estimate yield performance of a particular crop based on soil test results, environmental factors, the historic application of crop inputs, and historic yield of a previous crop to determine the timing and amount of application of the crop inputs. Crop inputs may include nutrients, such as fertilizer, nitrogen, phosphorous, potassium, and trace elements and minerals. Other crop inputs include pesticides, insecticides, herbicides, chemicals, plant hormones, water, irrigation, and other treatments for vegetation or soil.

To minimize the risks of insufficient nutrients, excessive weeds, or insect attacks on crop yields, growers may tend to over-apply fertilizer, herbicides, insecticides, respectively, to crops in an effort to maintain consistently high yields. However, the over-application of crop inputs may raise production costs and cause pollution of surface and ground water aquifers.

The Risk Management Agency, which is associated with the U.S. Department of Agriculture, may approve one or more endorsements (e.g., a Nutrient Best Management Practices (BMP) Endorsement) for crop insurance products based on preferential growing practices. Regulators outside of the U.S. may offer crop insurance products that are based on preferential growing practices. Although most growers are honest and operate with integrity, such endorsements may be vulnerable to fraudulent activities or negligence of the grower's personnel. Using traditional in-person monitoring and inspection may be difficult, costly or impractical because of the geographic scope of arable land. Accordingly, there is need for improved process for risk management on the application of crop inputs to facilitate pragmatic new crop insurance products and/or to facilitate growing crops with particular traits.

SUMMARY OF THE INVENTION

A system and method for managing a crop insurance program facilitates determining an input management plan for application of a crop input to a field within a defined geographic area. A field yield is measured. The field yield pertains to a yield of particular crop associated with a field in a defined geographic area. An aggregate yield is estimated. The aggregate yield relates to the particular crop associated with the defined geographic area. The aggregate yield is scaled to represent a generally equivalent land area to the field. A difference or variation is determined between the field yield and the aggregate yield. The determined difference or indication thereof is made available to a receiving entity (e.g., insurer that is associated with at least one of claims and insurance on the crop in the field).

DESCRIPTION OF THE PREFERRED EMBODIMENT

Figure 1:
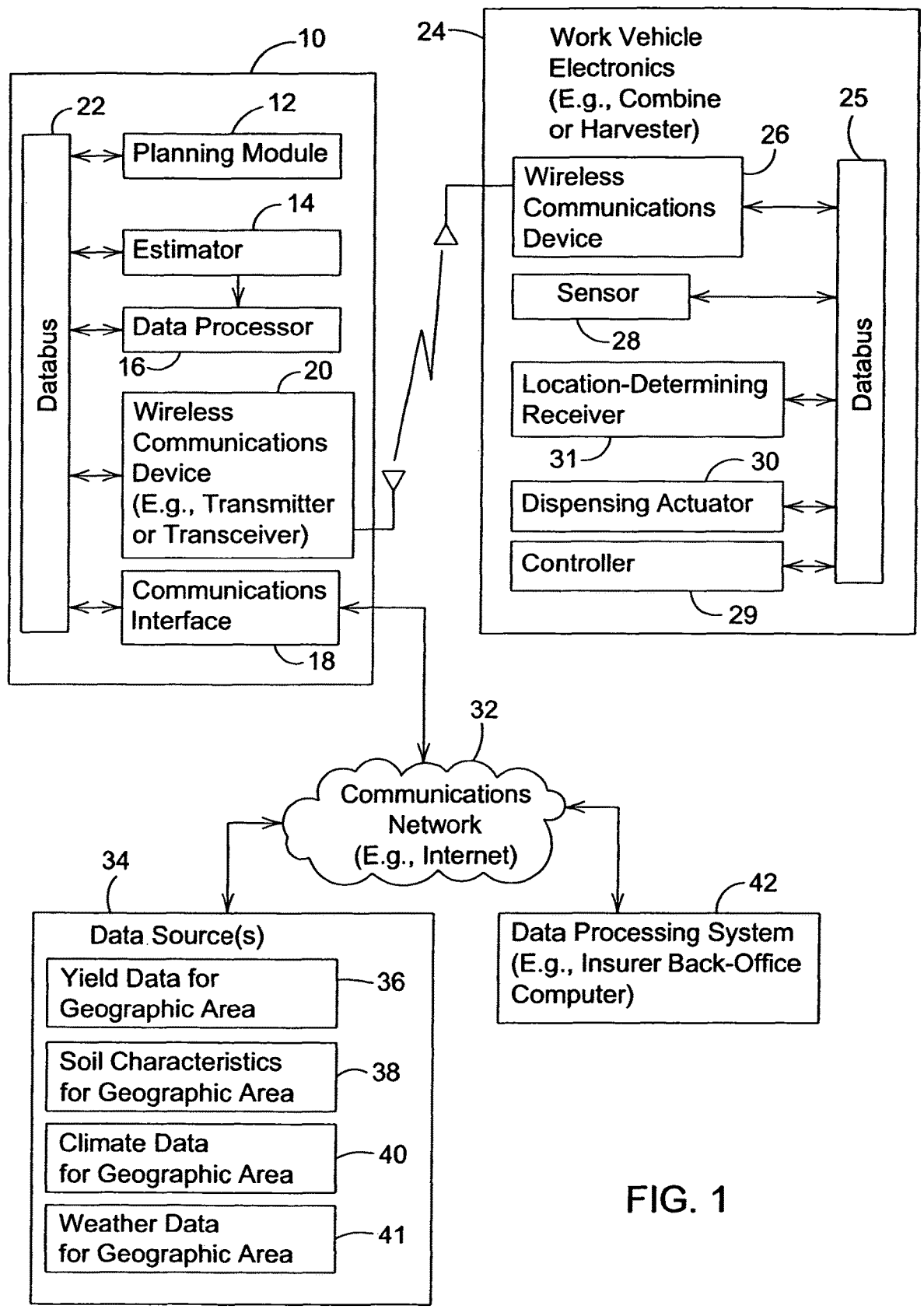
FIG. 1 is a block diagram of one embodiment of a system for managing a crop insurance program or grower compliance plan.

In FIG. 1 the system for managing a crop insurance program or grower compliance plan comprises work vehicle electronics 24 that communicates field input data to a data processing system 10 via an electromagnetic signal or otherwise. As used herein, a crop input management plan comprises a plan consistent with a crop insurance program, a grower compliance plan consistent with a contractual obligation of a grower, or both. One or more data sources 34 may communicate aggregate field input data for a defined geographic area to the data processing system 10 via a communications network 32 (e.g., the Internet) or another communications link. The data sources 34 may provide one or more of the following input data: yield data for a geographic area 36, soil characteristics for a geographic area 38, climate data for a geographic area 40, weather data for a geographic area 41, or other agronomic, topographical, geological, meteorological, or agricultural data that is commercially available, publicly available, or made available by any government or agency affiliated therewith.

The geographic area comprises one or more of the following: a country, a state, a county, a province, a canton, a region, a weather growing zone, a rainfall zone, a climate zone, a user definable zone, and a soil parameter zone. The geographic area may include or encompass the field (e.g., the geographic boundaries of the field) or the geographic area may share a substantially similar analogous climate, weather, growing degree days, growing zone, duration of growing season, and other agronomic characteristics.

The data processing system 10 comprises the following modules: a planning module 12, an estimator 14, a data processor 16, a communications interface 18, and a wireless communications device 20. In one embodiment, two or more of the foregoing modules may communicate with each other via a databus 22. In an alternate embodiment, two or more of the modules (12, 14, 16, 18 and 20) may communicate with each other via a logical data path, a physical data path, or both (e.g., in a distributed architecture). The planning module 12 determines an input management plan for application of a crop input to a field within or related to a defined geographic area. The sensor 28, associated with the work vehicle electronics 24, measures a first yield per land unit of a particular crop associated with the field. The estimator 14 of the data processing system 10 estimates a second yield per land unit of the particular crop associated with the defined geographic area. The defined geographic area may refer to one or more of the following: a country, a state, a county, a province, a canton, a region, a weather growing zone, a rainfall zone, a climate zone and a soil parameter zone. It is possible to define the defined geographic area (a) to be representative of (e.g., or substantially similar to) the weather, climate, growing zone, rainfall zone, and/or soil parameter zone of the field and (b) to be greater in size (e.g., acreage) than the field. The particular crop may include grain, oilseed, fiber, cotton, corn, soybeans, wheat, rice, barley, oats, flax, vegetables, fruits, edible plants, inedible plants, food crops, or any other crop. The data processor 16 determines a difference or variation between the first yield and the second yield. A communications interface 18 makes available (a) the determined difference or an indicator based thereon and (b) an identifier (e.g., a field identifier or grower identifier associated with the field) to a data processing system 42 (e.g., an insurer back-office computer) of a receiving entity (e.g., of an insurer). The receiving entity may represent a regulator, a governmental entity, or another person or business that is associated with at least one of claims and insurance on the field. The indicator may indicate whether the first yield meets, falls below, or exceeds expectations with respect to the second yield or another performance metric or standard. A grower identifier may indicate the name of a grower, a name of the grower's business, the grower's street address or the field's geographic coordinates, for example. The grower may contractually consent to the use of the grower identifier and related information incidental to the purchase of a crop insurance policy.

In one embodiment, the communications interface 18 device comprises a transmitter, a transceiver, a network interface module, a wireline communications device, a modem, a cable modem. The communications interface 18 is configured to transmit the difference or the indicator electronically to a data processing system 42 of an insurer, or another person or entity. The communications interface 18 may include communications software such as a web browser or support software for supporting hardware associated with the communications interface 18. Although an Internet Service Provider (ISP) is not shown, in an alternate embodiment an ISP may be interposed between the communications interface 18 and the communications network 32 (e.g., Internet).

The communications interface 18 may transmit the difference or the indicator to an insurer if the first yield and the second yield differs by more than a minimum threshold percentage. The minimum threshold percentage may be determined by an insurer, an insured, an insurance underwriter, risk evaluation, historic claims, a government regulator, the Risk Management Agency, the U.S. Department of Agriculture, or a combination of the foregoing, for example. Although other minimum thresholds fall within the scope of the invention, in one example the minimum threshold percentage is approximately five percent.

The work vehicle electronics 24 comprises the following elements: a controller 29, a sensor 28, a dispensing actuator 30, a location-determining receiver 31, and a wireless communications device 26. Two or more of the foregoing elements may communicate with one another via the databus 25 or another physical or logical data path. The sensor 28 may be used to sense the yield, volume, weight, or quantity of a particular crop or a harvested agricultural product (e.g., grain, oilseed, or fiber). The sensor 28 or controller 29 may include data processing for determining a yield per unit land for a field in which the work vehicle operates. The location-determining receiver 31 may comprise a Global Positioning System (GPS) receiver for determining the location of the work vehicle, estimating ground speed of the work vehicle for yield determination, and determining whether the vehicle is located within a particular field or subfield region thereof.

As the crop in a field is harvested, the location-determining receiver 31 provides location data to determine that the harvested crop is associated with the proper corresponding field (or subfield geographic location or region) in which it was grown. The controller may compare the location data outputted from the location-determining receiver 31 during harvesting to the reference location data associated with boundaries of the field to determine whether or not the work vehicle is harvesting in the field (or subfield geographic location or region).

The controller 29 may instruct the dispensing actuator 30 to meter or control the volume, rate, weight or quantity of an agricultural input dispensed or distributed within the field or subfield region. For example, a crop input may include a nutrient, fertilizer, a micronutrient, a mineral, a trace element, insecticide, pesticide, herbicide, fungicide, plant hormone, insect bacteria, insect virus, water, chemicals, manure, acid, alkaline material, a pH-balancing additive (e.g., lime stone powder), or other input that may be applied to a field.

The sensor 28 comprises at least one of a mass sensor, a weight sensor, flow sensor, a moisture sensor, a piezoelectric transducer, a grain flow sensor, a grain moisture sensor, a ground speed sensor, a header position switch, an impact force sensor, a plate displacement sensor, a volume measurement device, a load cell system, a radiometric system, and a capacitance sensor. In one illustrative example, the sensor 28 is mounted in the path of crop flow (e.g., grain flow) within the work vehicle (e.g., combine or harvester). The sensor 28 detects the first yield per land unit for a harvester, a combine, or another work vehicle. The wireless communications device 26 (of the work vehicle electronics 24) is arranged to transmit the measured data relating to the first yield per land unit to a wireless communications device 20 (of the data processing system 10) via an electromagnetic signal.

Although other configurations are possible, the sensor 28 may include a movable member (e.g., a plate) that is associated with the path of harvested agricultural product and mounted via a piezoelectric transducer or another electromechanical device for measuring force or displacement associated with the flow of the agricultural product (e.g., grain). During operation of the sensor 28, the movable member is displaced by the flow of agricultural product (e.g., grain) associated with a harvester, combine or other agricultural equipment such that the amount of displacement or force measured by a piezoelectric transducer indicates the quantity, volume, or weight of harvested grain. Further, in one embodiment, sensor 28 may include an optional moisture detector for measuring the moisture content of the grain. The moisture detector may comprise capacitive plates or probes that are associated with the path of harvested agricultural product. Each range or level of moisture in the agricultural product is associated with a corresponding capacitance range or level between the capacitive probes. The weight, volume or quantity determined by the electrical energy produced by the electrical transducer (or other device for measuring force or displacement of the sensor 28) is adjusted to compensate for grain moisture to accurately determine the yield of a particular crop. The moisture compensation determined by the capacitance may vary, and may be subject to further correction, depending upon the type or variety of grain grown, the amount of rainfall during the growing season, the time of day of harvesting, ambient humidity during harvesting, weather conditions during harvesting, and other factors, for example.

The insurance management system of FIG. 1 may be applied to managing an insurance policy or endorsement for yield-monitored crop insurance, Best Management Practices (BMP) crop insurance, another form of crop insurance, or risk management of growing practices.

Figure 2:
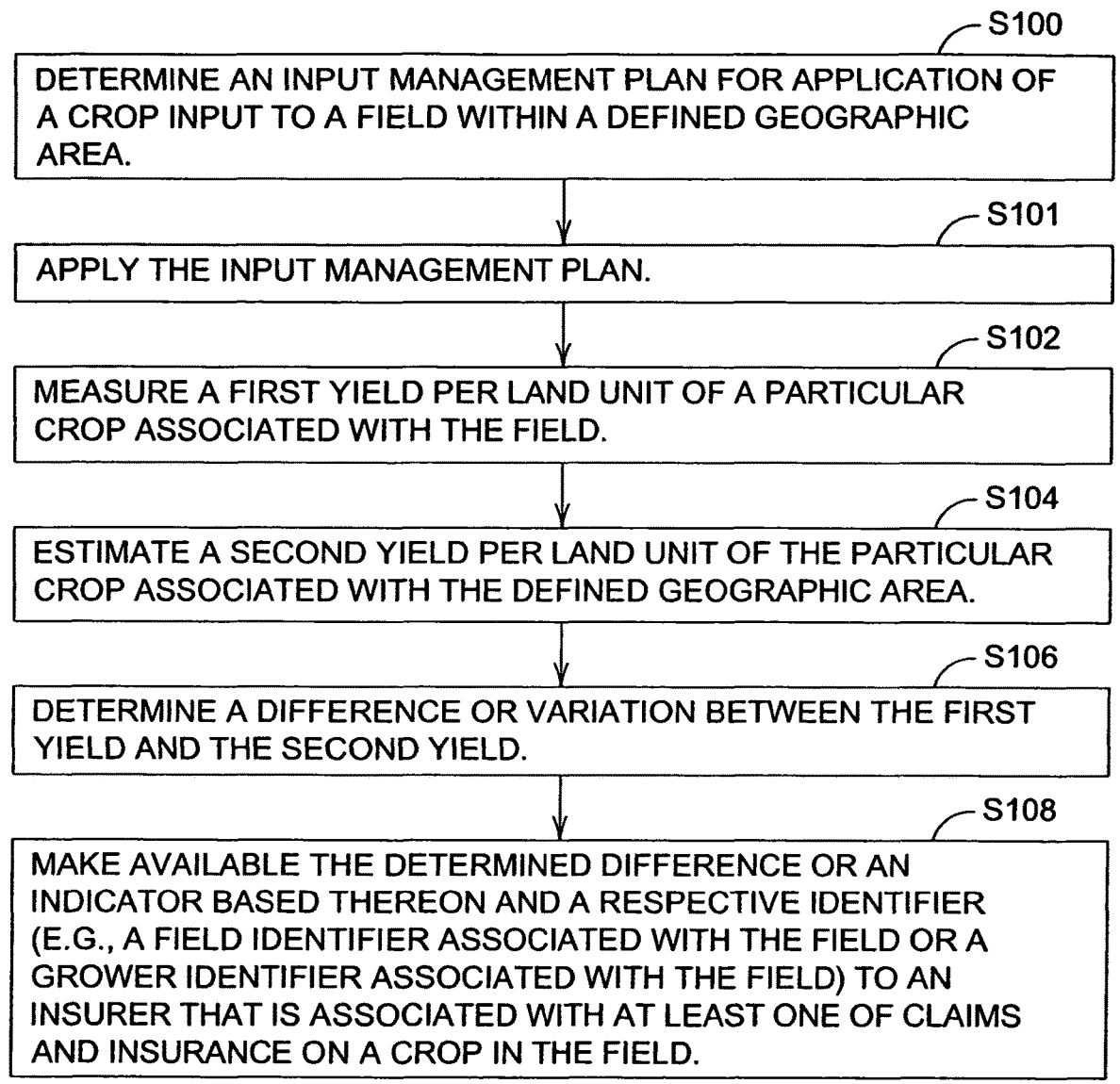
FIG. 2 is a flow chart of one example of a method for managing a crop insurance program or grower compliance plan.

FIG. 2 discloses a method for managing a crop insurance program or a grower compliance plan. A grower compliance plan may be associated with a contractual requirement between a grower and a potential purchaser of a grower's output conditional upon the grower's output being substantially compliant to a grower compliance plan. The grower compliance plan may require a particular crop to have a certain characteristic or trait, or a certain characteristic (e.g., protein content or oil content of the crop) and a corresponding level or range (e.g., greater than a certain percent by volume or weight of the crop) for such characteristic. The method of FIG. 2 begins in step S100.

In step S100, a planning module 12, a consultant, or a qualified person determines an input management plan for application of a crop input to a field within a defined geographic area. The qualified person may have specialized experience, skill, training, formal education, or certification, for example in providing advice or consultation on the preparation and recommendation of a crop input management plan. In general, the geographic area may comprise one or more of the following: a country, a state, a county, a province, a canton, a region, a weather growing zone, a rainfall zone, a climate zone, and a soil parameter zone. In one embodiment, the geographic area is greater in geographic scope than the field and substantially similar to one or more characteristics (e.g., weather, climate, soil, growing degree days, endemic insect populations, plant disease rates and frequencies) of the field. In one example, the input plan may comprise the following plan components: a time window, quantity, and concentration of nitrogen fertilizer to be applied to a particular field for a corresponding crop.

In step S101, the determined input management plan is applied. The input management plan may be implemented by a work vehicle equipped with work vehicle electronics 24 for the controlled distribution or dispensation of one or more crop inputs. For example, the determined input plan may apply a crop input (e.g., nitrogen) consistent with a preferential rate (e.g., concentration), temporal window (date of application), and specification (e.g., solubility in an aqueous solution within a defined tolerance) to a geographic area on a field or sub-field basis.

In step S102, a sensor 28 or work vehicle electronics 24 measures a first yield per land unit of a particular crop associated with the field. The sensor 28 may comprise one or more of the following components: a mass sensor, a weight sensor, flow sensor, a moisture sensor, a piezoelectric transducer, a grain flow sensor, a grain moisture sensor, a ground speed sensor, a header position switch, an impact force sensor, a plate displacement sensor, a volume measurement device, a load cell system, a radiometric system, and a capacitance sensor. The measuring of the first yield per land unit comprises detecting the first yield per land unit at a harvester, a combine, or a work vehicle and transmitting the first yield per land unit to a data processing system 10 via an electromagnetic signal.

In step S104, an estimator 14 estimates a second yield per land unit of the particular crop associated with the defined geographic area. The estimator 14 may estimate the second yield in accordance with various techniques that may be applied alternately or cumulatively. Under a first technique, the estimator 14 estimates the second yield excluding the yields associated with compliant fields (e.g., compliance with insurance policy requirements or contractual grower requirements or a crop management plan) within the geographic area that follow the management plan. Under a second technique, the estimator 14 estimates the second yield excluding the yields associated with noncompliant fields (e.g., noncompliant with insurance policy requirements or contractual grower requirements or a crop management plan) within the geographic area that do not follow the management plan.

In step S106, a data processor 16 determines a difference or variation between the first yield and the second yield. For example, the difference may be expressed as a volumetric difference, a weight difference, bushels, bushels per acre, weight per acre, net weight (e.g., gross weight minus tare weight) or otherwise.

In step S108, a communications device makes available (a) the determined difference, or an indicator based thereon, and (b) a respective identifier to a receiving entity. The identifier may comprise a field identifier of a field or a grower identifier for grower associated with the crop. The receiving entity is any person, business, or governmental entity with an interest in the grower's compliance with a crop insurance policy or other contractual obligation. For example, the receiving entity may represent an insurer that is associated with at least one of claims and insurance on the field. Alternatively, the receiving entity may represent a purchaser of the growers crop or a portion thereof.

In step S108, the making available of the determined difference information may be accomplished in accordance with various alternate procedures. Under a first procedure, the making available comprises transmitting the difference electronically to an insurer (e.g., its back office computer). Under a second procedure, the making available comprises transmitting the difference to an insurer if the first yield and the second yield differs by more than a minimum threshold percentage. Although other minimum threshold percentages that are greater or less may fall within the scope of the invention, in one embodiment, the minimum threshold percentage is approximately five percent.

Figure 3:
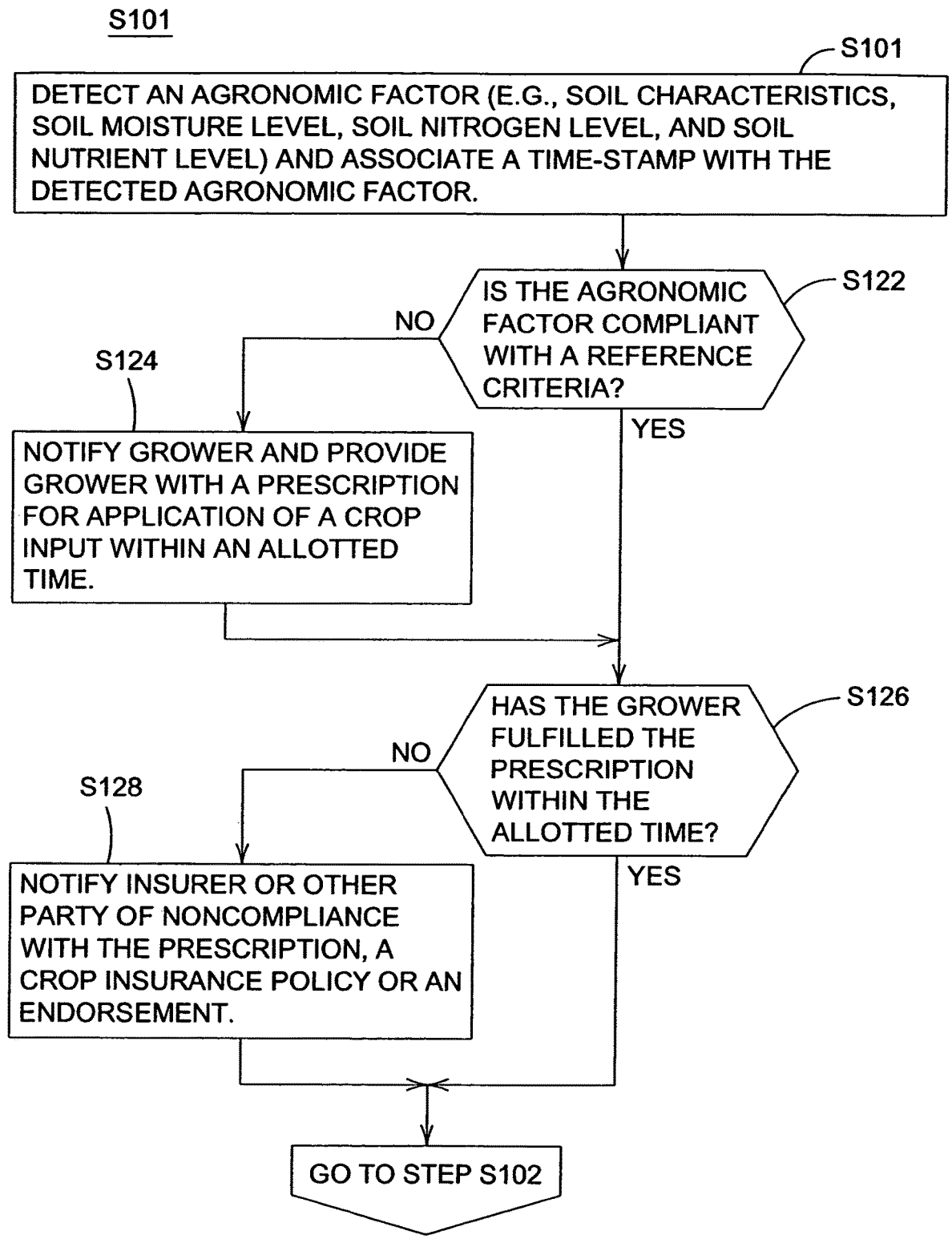
FIG. 3 shows the application of an input management plan in greater detail than FIG. 2.

The procedure of FIG. 3 shows step S101 of FIG. 2 in greater detail.

In step S120, a sensing station 50 (FIG. 9) or a sensor 28 detects an agronomic factor and associates the agronomic factor with a corresponding time stamp. An agronomic factor comprises one or more of the following: soil characteristics, soil moisture level, soil nitrogen level, and soil nutrient level.

In step S122, a sensing station 50, controller 29, or data processor 16 determines if an agronomic factor is compliant with a reference criteria. If the agronomic factor is not compliant, the method continues with step S124. However, if the agronomic factor is compliant, the method continues with step S126.

In step S124, the grower is notified and provided with a prescription (e.g., a warning, instructions, or other notification) for application of a crop input within an allotted time. In a first example, the user interface 48 (FIG. 7) of a crop input planning system 46 displays or provides a user with a prescription for application of a crop input within an allotted time. In a second example, the work vehicle electronics 24 determines a prescription for application of the crop input within the allotted time based on agronomic data of the sensor 28 or the sensing station 50. The work vehicle electronics 24 may display the prescription or merely provide input data to the dispensing actuator 30 to carry out the prescription. In a third example, the planning module 12 develops a prescription based on the agronomic factor from a sensing station 50 or sensor 28 and electromagnetically transmits such prescription to the work vehicle electronics 24 in electronic form (e.g., a data file of crop input identifier, and rate versus location data).

In step S126, the sensing station 50, the data processor 16, or the work vehicle electronics 24 determines if the grower has fulfilled the prescription within the allotted time. If the grower has fulfilled the prescription within the allotted time, the method continues with step S102 of FIG. 2, for example. However, if the grower has not fulfilled the prescription within the allotted time, the method continues with step S128.

In step S128, the data processing system notifies an insurer or other party of noncompliance with the prescription, a crop insurance policy or an endorsement via a communications network 32 or otherwise. For example, the data processing system 10 may send a data message to the data processing system 42 (e.g., insurer back-office computer) via the communications network 32 (e.g., a data packet network or Internet) or another communications link. The data message is directed or addressed to the data processing system 42.

Figure 4:
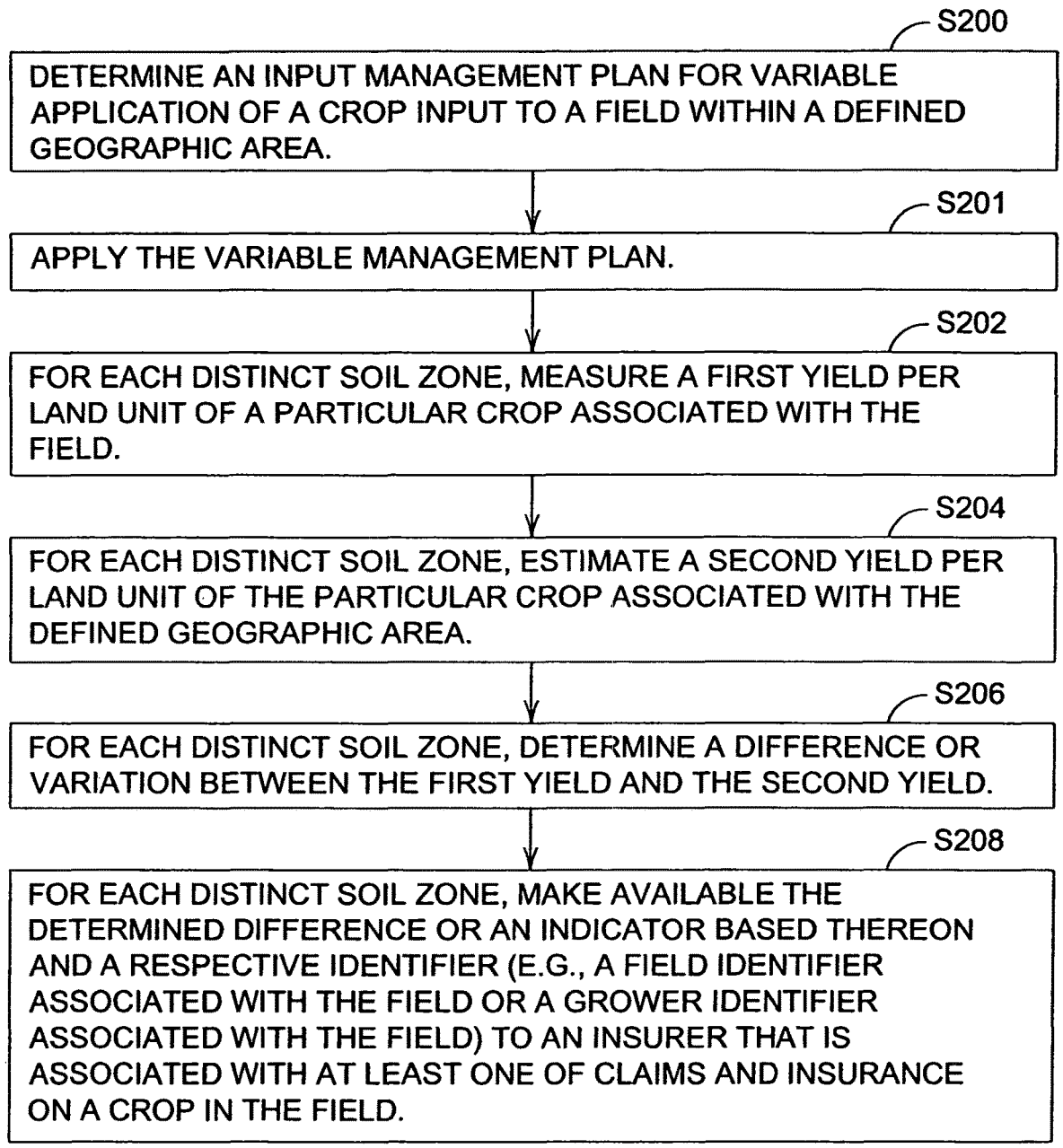
FIG. 4 is a flow chart of another example of a method for managing a crop insurance program or a grower compliance plan.

FIG. 4 shows an alternate method of managing a insurance program or a grower compliance program. The method of FIG. 4 begins in step S200.

In step S200, a planning module 12, a consultant, or a qualified person determines a variable input management plan for variable application of a crop input to a field within a defined geographic area. The field may be subdivided into materially distinct soil zones such that each distinct soil zone can receive specialized or disparate treatment (e.g., variable application of crop inputs) to maximum crop performance or yield across an entire field. The qualified person may have specialized experience, skill, training, formal education, or certification, for example in providing advice or consultation on the preparation and recommendation of a crop input management plan. In one example, the geographic area comprises one or more of the following: a country, a state, a county, a province, a canton, a region, a weather growing zone, a rainfall zone, a climate zone, and a soil parameter zone.

In step S201, the determined variable input management plan is applied. The variable input management plan may be implemented by a work vehicle equipped with work vehicle electronics 24 for the controlled distribution or dispensation of one or more crop inputs to various soil zones within the field. For example, the determined variable input plan may apply a crop input (e.g., nitrogen) consistent with a preferential variable rate versus location within a field or subfield region, temporal window (e.g., date of application), and specification (e.g., solubility) to a geographic area on a field or sub-field basis.

In step S202, a sensor 28 or work vehicle electronics 24 measures a first yield per land unit of a particular crop associated with the field in or more distinct soil zones. For example, each distinct soil zone within the field may be associated with a corresponding yield or yield range for the particular crop. The measuring of the first yield per land unit comprises detecting the first yield per land unit at a harvester, a combine, or a work vehicle and transmitting the first yield per land unit in or more distinct soil zones to a data processing system 10 via an electromagnetic signal or otherwise.

In step S204, for each distinct soil zone, an estimator 14 estimates a second yield per land unit of the particular crop associated with the defined geographic area. The estimator 14 may estimate the second yield in accordance with various techniques that may be applied alternately or cumulatively. Under a first technique, the estimator 14 estimates the second yield excluding the yields associated with compliant fields (e.g., compliance with insurance policy requirements or contractual grower requirements or a crop management plan) within the geographic area that follows the input management plan or a substantially similar input management plan. Under a second technique, the estimator 14 estimates the second yield excluding the yields associated with noncompliant fields (e.g., noncompliant with insurance policy requirements or contractual grower requirements or a crop management plan) within the geographic area that does not follow the input management plan or a substantially similar input management plan.

In step S206, for each distinct soil zone, a data processor 16 determines a difference or variation between the first yield and the second yield. For example, the difference may be expressed as a volumetric difference, a weight difference, bushels, bushels per acre, weight per acre, a net weight, or otherwise.

In step S208, for each distinct soil zone, a communications device (e.g., communications interface 18) makes available the determined difference and a respective identifier to a receiving entity that is an interest in the growers compliance with a contractual obligation associated with the crop in the field. The identifier may represent a field identifier or a grower identifier associated with the field. The receiving entity may represent an insurer that is associated with at least one of claims and insurance on the field. Alternatively, the party may represent a purchaser of the grower's crop or a portion thereof.

In step S208, the making available of the determined difference information may be accomplished in accordance with various alternate procedures. Under a first procedure, the making available comprises transmitting the difference electronically to an insurer. Under a second procedure, the making available comprises transmitting the difference to an insurer if the first yield and the second yield differs by more than a minimum threshold percentage. Although other minimum threshold percentages that are greater or less may fall within the scope of the invention, in one embodiment, the minimum threshold percentage is approximately five percent.

Figure 5:
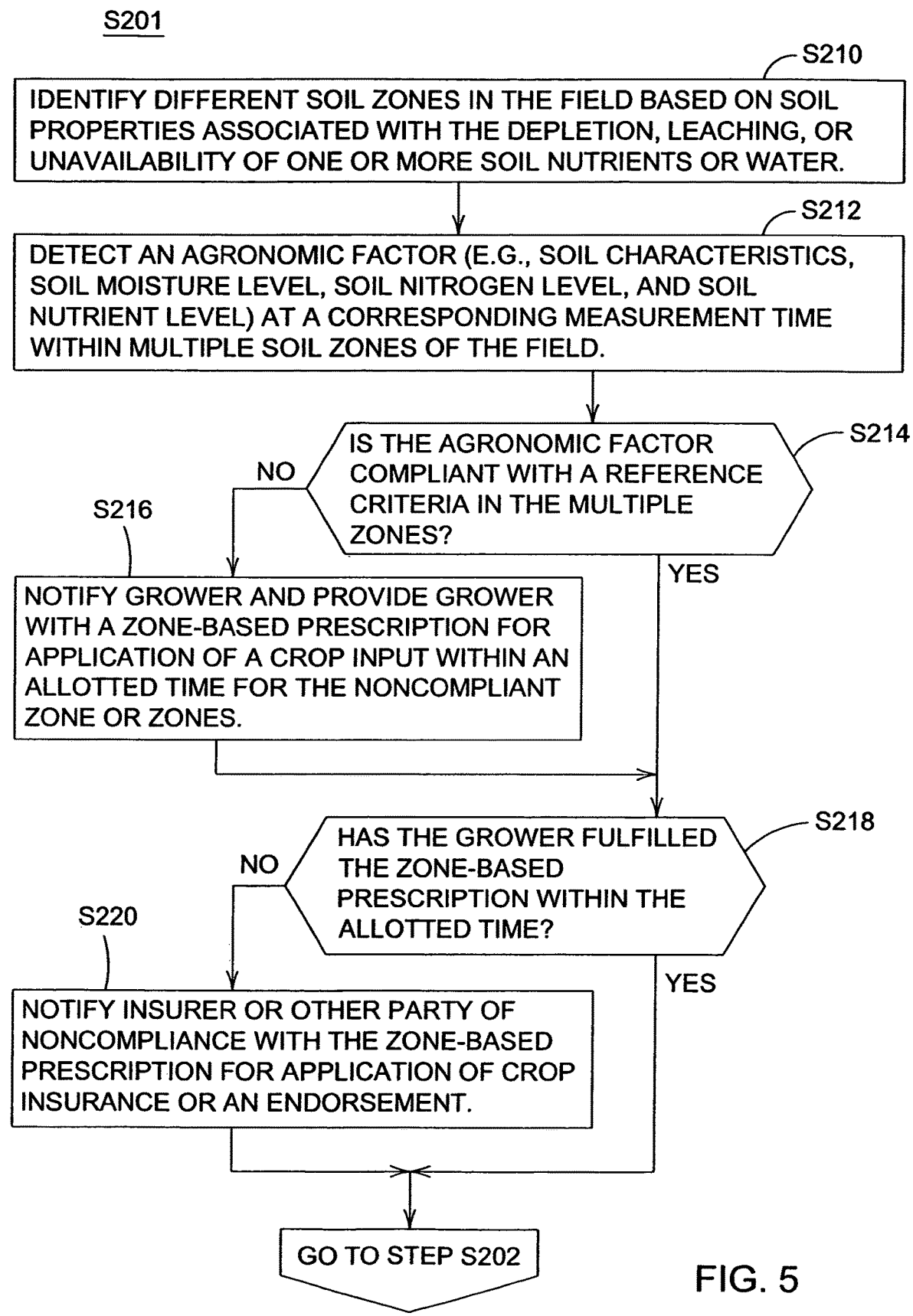
FIG. 5 shows the application of an input management plan in greater detail than FIG. 4.

The procedure of FIG. 5 shows step S201 of FIG. 4 in greater detail.

In step S210, different soil zones are identified in a field based on soil properties associated with the depletion, leaching, availability, or unavailability of one or more soil nutrients or water.

In step S212, a sensing station 50 (FIG. 9) or a sensor 28 detects an agronomic factor (e.g., soil characteristics, soil moisture level, soil nitrogen level, and soil nutrient level) at a corresponding measurement time (e.g., a time stamp) within the identified different soil zones in the field. An agronomic factor comprises one or more of the following: soil characteristics, soil moisture level, soil nitrogen level, and soil nutrient level.

In step S214, a sensing station 50, controller 29, or data processor 16 determines if an agronomic factor is compliant with a reference criteria in one or more of the multiple soil zones. In one example, under a first reference criteria sensing stations 50 determine if an agronomic factor is compliant with a reference criteria in a majority of the multiple soil zones. In a second example, under a second reference criteria sensing stations 50 determine if an agronomic factor is compliant with a reference criteria over all soil zones. If the agronomic factor is not compliant in one or more of the multiple soil zones in accordance with the first reference criteria and the second reference criteria, the method continues with step S216. However, if the agronomic factor is compliant in all of the soil zones, the method continues with step S218.

In step S216, the grower is notified and provided with a zone-based prescription for application of a crop input within an allotted time for the noncompliant zone or zones. In one example, the user interface 48 (FIG. 7) of a crop input planning system 46 displays or provides a user with a zone-based prescription for application of a crop input within an allotted time. In another example, the work vehicle electronics 24 determines a zone-based prescription for application of the crop input within the allotted time. The work vehicle electronics 24 may display the prescription or merely provide input data to the dispensing actuator 30 to carry out the zone-based prescription.

In step S218, the sensing station 50, the data processor 16, or the work vehicle electronics 24 determines if the grower has fulfilled the zone-based prescription within the allotted time. If the grower has fulfilled the prescription within the allotted time, the method continues with step S202 of FIG. 4, for example. However, if the grower has not fulfilled the prescription within the allotted time, the method continues with step S220.

In step S220, the data processing system 10 notifies an insurer or other party of noncompliance with the zone-based prescription, a crop insurance policy or an endorsement via a communications network 32 or otherwise. For example, the data processing system 10 may send a data message to the data processing system 42 (e.g., insurer back-office computer) via the communications network 32 (e.g., a data packet network or Internet) or another communications link.

Figure 6:
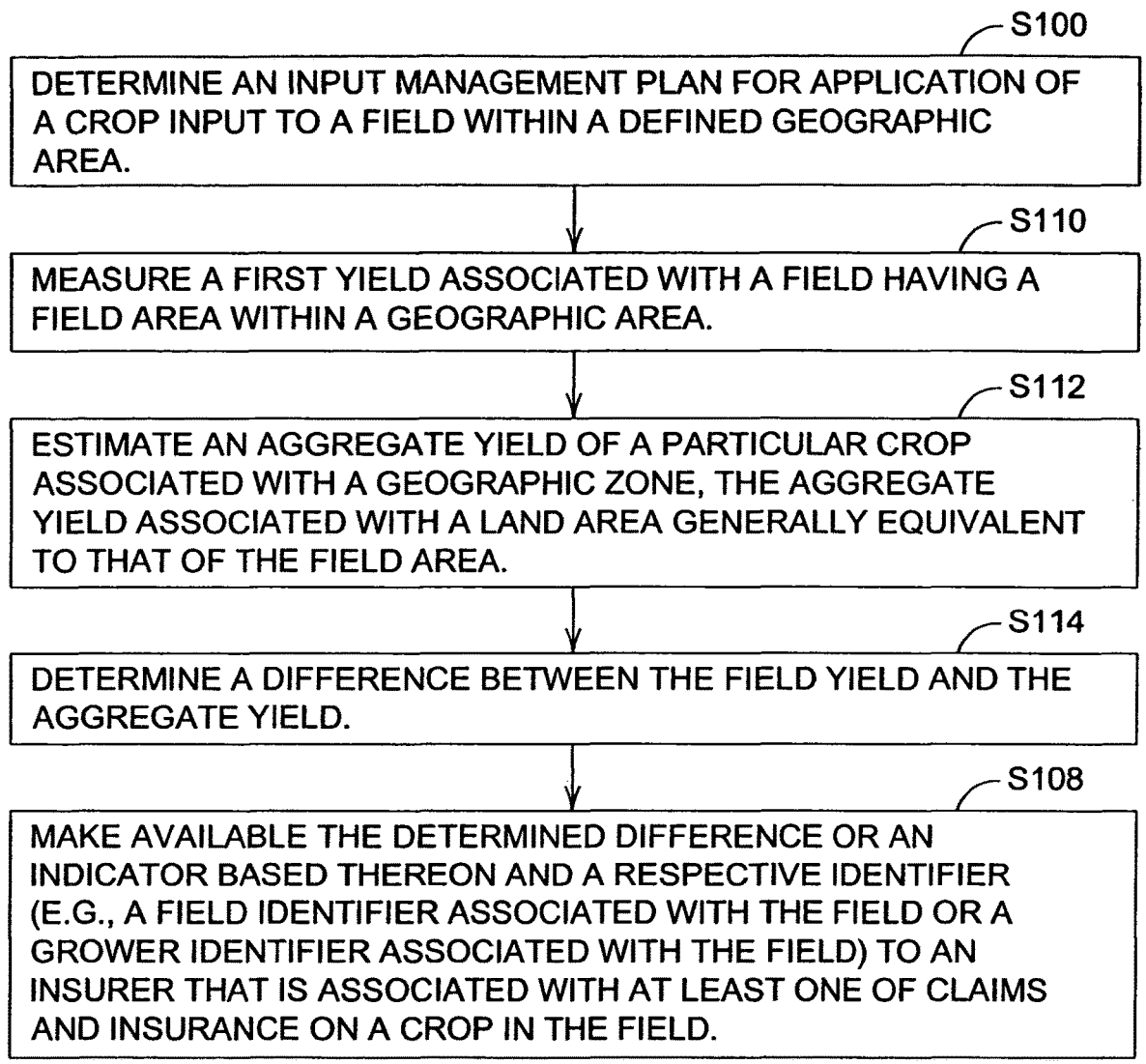
FIG. 6 is a flow chart of yet another example of a method for managing a crop insurance program or grower compliance plan.

FIG. 6 shows an alternate method of managing a insurance program or a grower compliance program. The method of FIG. 6 begins in step S100.

In step S100, a planning module 12, a consultant, or a qualified person determines an input management plan for application of a crop input to a field within a defined geographic area. The qualified person may have specialized experience, skill, training, formal education, or certification, for example in providing advice or consultation on the preparation and recommendation of a crop input management plan. The geographic area comprises one or more of the following: a country, a state, a county, a province, a canton, a region, a weather growing zone, a rainfall zone, a climate zone, and a soil parameter zone.

In step S110, a sensor 28 measures or facilitates the determination of a field yield associated with a field having a field area within a geographic area.

In step S112, an estimator 14 estimates an aggregate yield of a particular crop associated with a geographic zone. The aggregate yield is associated with a land area generally equivalent to that of the field area.

In step S114, a data processor 16 determines a difference between the field yield and the aggregate yield.

In step S108, a communications interface 18 makes available the determined difference and a field identifier associated with the field to an insurer, governmental regulator, or other entity that is associated with at least one of claims and insurance on the field.

Figure 7:
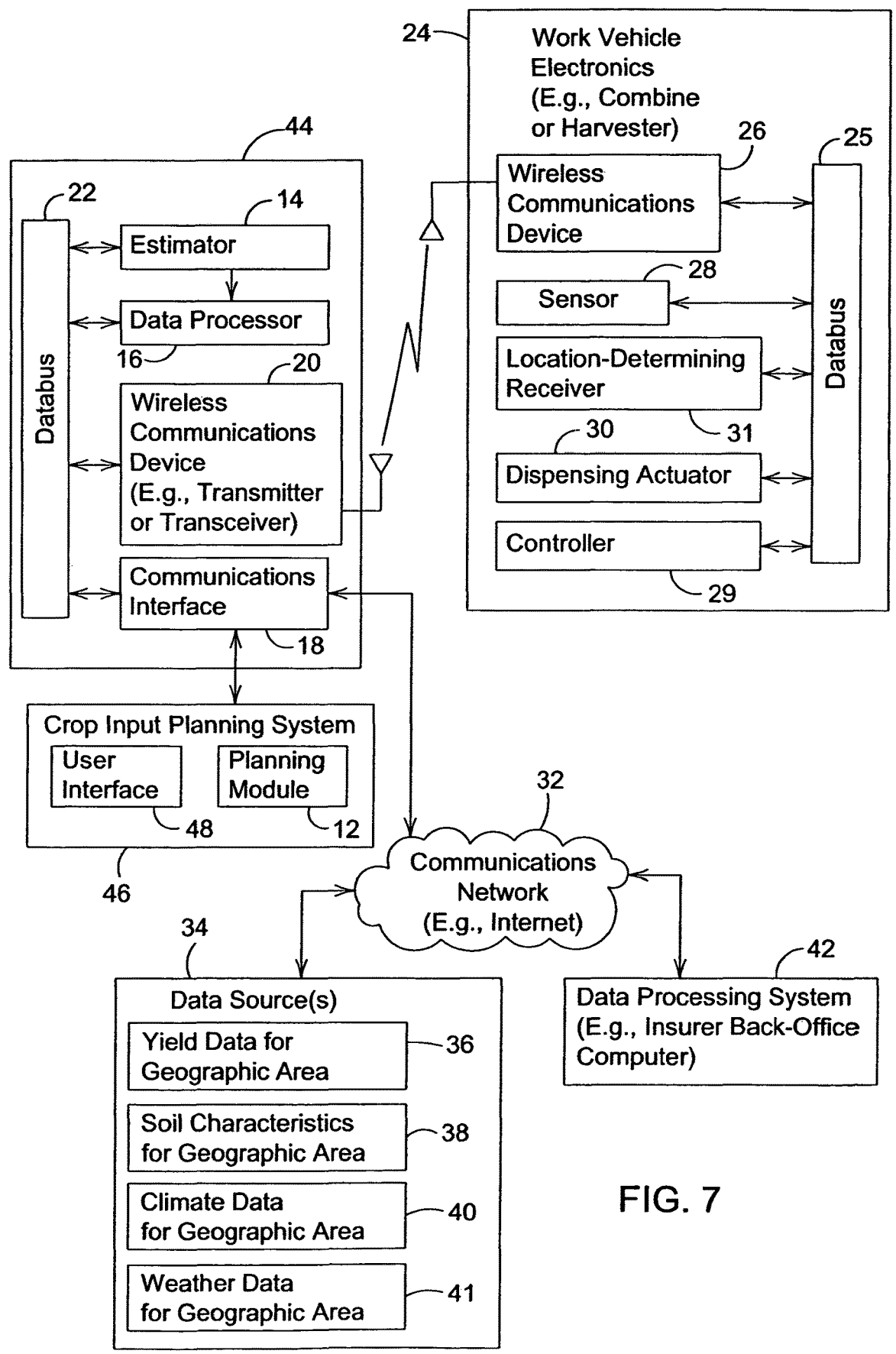
FIG. 7 is a block diagram of another embodiment of a system for managing a crop insurance program or grower compliance plan.

FIG. 7 shows an alternate embodiment of a block diagram of a system for managing an insurance program or a grower compliance program. The system of FIG. 7 is similar to the system of FIG. 1 except the system of FIG. 7 has a different data processing system 44 without an integral planning module 12 resident therein. Instead, the planning module 12 is associated with a crop input planning system 46.

The crop input planning system 46 may comprise a user interface 48 and a planning module 12. The user interface 48 may support a user inputting data, outputting data, entering commands, or otherwise interacting with the crop input planning system 46.

The crop input planning system 46 may be used to verify crop input recommendations from a consultant or qualified expert, to supplement such recommendations, or to deliver the crop input recommendations from the consultant or qualified expert. The crop input planning system 46 may output the crop input recommendations in a standard data format that is recognizable by the communications interface 18 of the data processing system 10. Further, the planning module 12 may support the preparation and arrangement of control commands for controlling the dispensing actuator 30 of the work vehicle electronics 24. The wireless communications device 20 of the data processing system 10 may communicate the control commands (or a data file representing such control commands) to the wireless communications device 20 of the work vehicle electronics 24 via an electromagnetic signal (e.g., radio frequency transmission, spread-spectrum transmission, any modulation scheme, encoding scheme, digital, or analog format licensed or unlicensed by the Federal Communications Commission or another governmental regulator).

Figure 8:
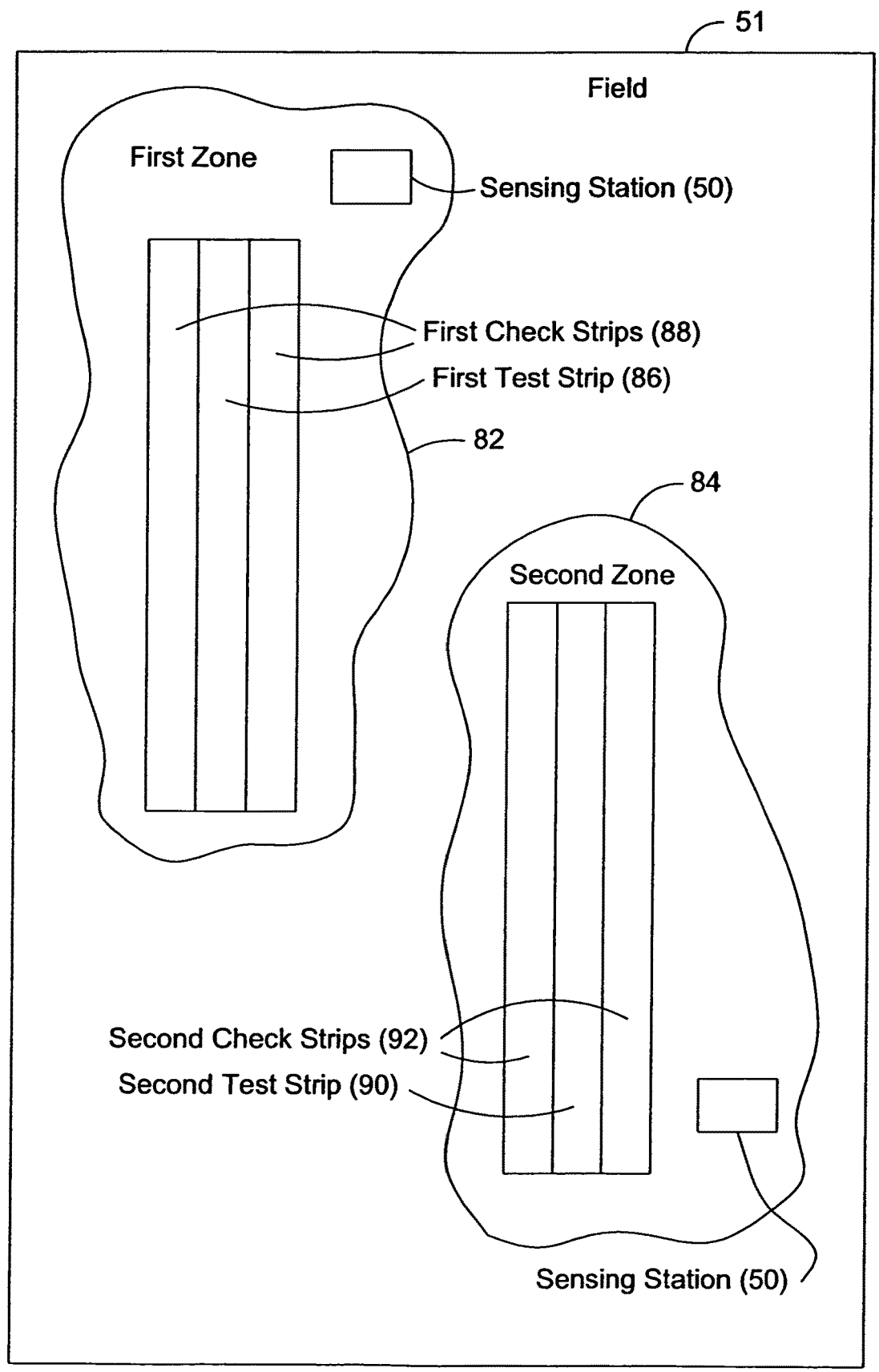
FIG. 8 is a plan view of an exemplary field with different test strips associated with corresponding zones of the field.

FIG. 8 shows a plan view of an illustrative field 51 in accordance with one embodiment. Other plan views and arrangements may fall within the scope of the claims. The illustrative field 51 may be used to carry out monitoring of a best management practices (BPM) program or program in which growers are given recommendations or prescriptions on growing crops in accordance with certain growing practices. The growing practices may arise from the desire to conserve in the amount of fertilizer, nutrients, pesticides, fungicides, herbicides, and other chemicals applied to crops to reduce the cost of agricultural inputs, preferably without materially reducing the yield of the crop. However, the growing practices may relate to growing specialty crops, pharmaceutical crops, genetically modified crops, organic crops, non-genetically modified crops, or crops with specific attributes to fulfill the terms of a contract for the purchase of the crops or to provide a crop that is compliant with some recognized standard.

In FIG. 8, soil survey data is used to develop two or more different zones within the field 51. As illustrated in the example of FIG. 8, the field 51 contains a first zone 82 and a second zone 84, but more zones per field are permitted, which may vary based on the size of the field, local terrain, and local soil characteristics, among other factors. In one embodiment, different zones (e.g., the first zone 82 and the second zone 84) are identified in the field 51 based on at least one of soil properties and previously grown crops. The zones are based on a crop history for the zone, a crop input history for the zone, a historic nutrient exposure of the zone, and a nutrient mobility rating associated with the zone, and a hydraulic mobility rating associated with the zone, and an irrigated zone versus a non-irrigated zone. In one embodiment, each zone may be selected to be generally representative of one or more respective remaining portions of the field 51 of greater land area than the corresponding zone itself.

In general, each zone may contain a test strip (e.g., a first test strip 86 and a second test strip 90) that is bounded by one or more check strips (e.g., a first check strip 88 and second check strip 92). The test strip is a region in which the grower can treat in accordance with the growers' own preferences to produce a higher yield or to fulfill an attribute specification or contract for a particular crop. The test strip is generally linear or curved such that a planter, tractor, or another work vehicle may physically traverse the path formed by the test strip. The check strips are treated in accordance with a prescription or recommendation provided by the planning module 12 or a qualified consultant.

As illustrated in FIG. 8, the first zone 82 contains a first test strip 86 and is bounded by adjacent check strips on both sides, which are referred to as the first check strips 88; the second zone 84 contains a second test strip 90 and is bounded by adjacent check strips on both sides, which are referred to as second test strips 92.

A consultant may supervise or administer the preferential growing practices (e.g., best management practices) for the check strips (e.g., the first check strips 88, the second check strips 92, or both). For example, the consultant may distribute crop inputs at particular times at particular dosages during or prior to a growing season for the crop. If the difference between the test strip and one of the check strips (e.g., at least one side of the first check strips 88 or the second check strips 92) varies by a material amount, the grower may be entitled to a payment of an insurance benefit, subject to the terms and conditions of any insurance policy granted on the performance of the crop.

In a first configuration, the difference between the test strip and the check strip must be present in majority of the zones before the grower may be entitled to a payment of an insurance benefit, among other requirements. Further, the yield associated with the test strip should be greater than the yield of the check strip by some material amount as a condition precedent to the payment of any insurance benefit to the insured.

In second configuration, the difference between the test strip and check strip must be present in all of the zones before the grower may be entitled to a payment of an insurance benefit, among other requirements. Further, the yield associated with the test strip should be greater than the yield of the check strip by some material amount as a condition precedent to the payment of any insurance benefit to the insured.

In a third configuration, the recommendation or prescription of the farmer may vary by zone, such that each zone is independent of the other zone with respect to whether or not the test strip is compliant or noncompliant, among other requirements. Further, the yield associated with the test strip should be greater than the yield of the check strip by some material amount as a condition precedent to the payment of any insurance benefit to the insured.

Each zone is associated with at least one sensing station 50. For example, the sensing station 50 may be positioned to collect data associated with a test strip, a check strip, or otherwise. The sensing station 50 may include at least one of a weather monitor 54, a soil moisture detector, and nutrient level detector.

The sensing station 50 may operate in accordance with several alternate or cumulative techniques. Under a first technique, the sensing station 50 may store historical sensor 28 data in the deployed remote sensors 28 and may communicate the stored sensor 28 data via an electromagnetic signal to a remote data processing system 10 upon interrogation, polling, at defined intervals, upon accumulation of a threshold amount of sensor data or otherwise. Under a second technique, the work vehicle electronics 24 may be mounted on a work vehicle (e.g., a harvester or a combine) for harvesting the particular crop. The work vehicle electronics 24 may interrogate the sensing station 50 during the harvesting process to gather from one day to an entire season of collected data. The collected data may be forwarded by the work vehicle electronics 24 to the data processing system 10 for further processing consistent therewith. The collected data may be analyzed or screened to determine if the grower may have engaged in fraud or other activities or noncompliant growing practices that materially depart from the crop input plan or qualified recommendations.

Figure 9:
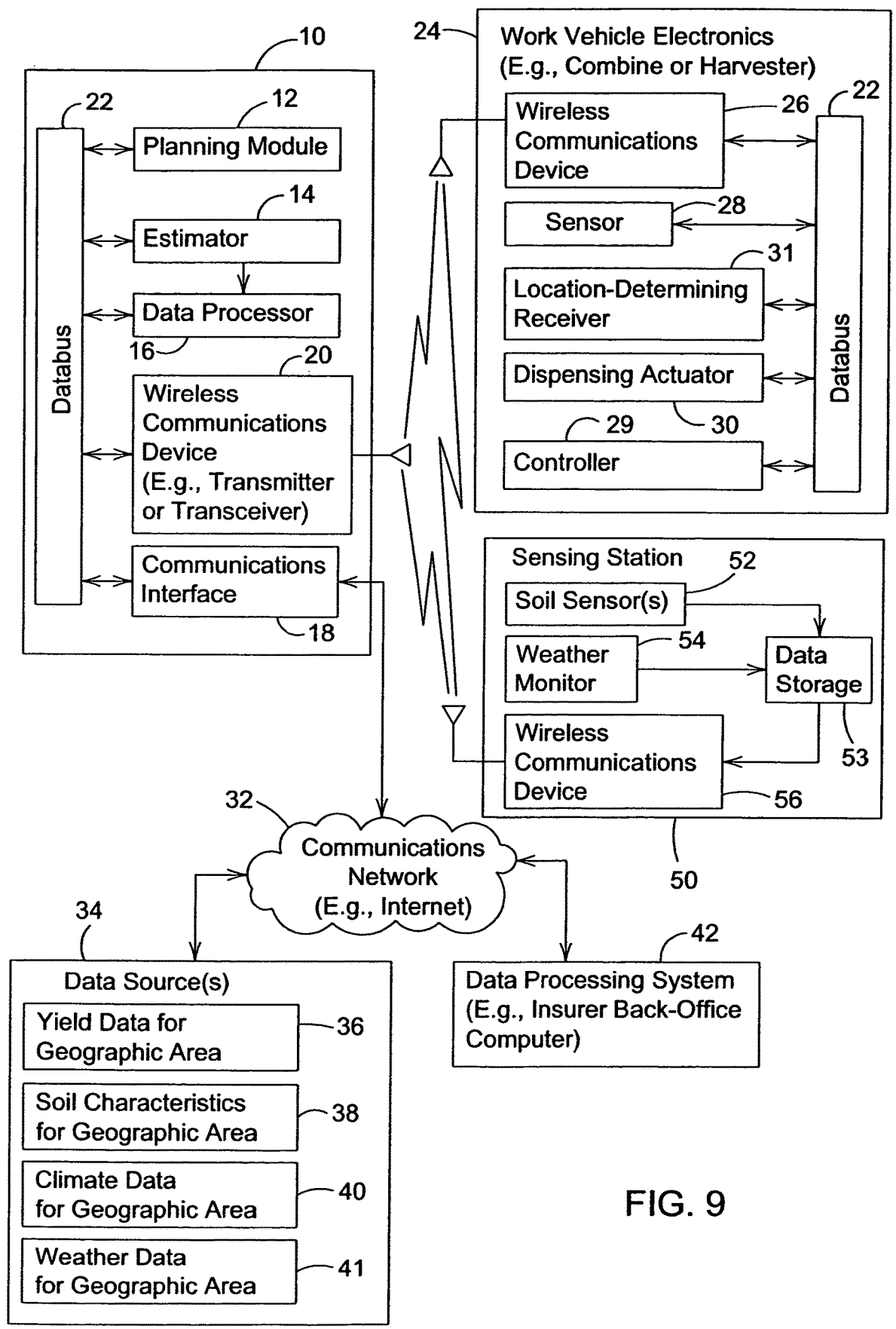
FIG. 9 is a block diagram of yet another embodiment of a system for managing a crop insurance program or grower compliance plan.

FIG. 9 shows a system that is similar to the system of FIG. 1, except the system of FIG. 9 further comprises one or more sensing stations 50. Like reference numbers indicate like elements in FIG. 1, FIG. 8, and FIG. 9.

The sensing station 50 comprises a soil sensor 52, a weather monitor 54, and a wireless communications device 56 (e.g., a transceiver or transmitter). Further, in the embodiment shown in FIG. 9, the sensing station 50 may further comprise a data storage device 53 for storing sensed data, soil data, weather data, soil moisture data, temperature data, barometric pressure data, rainfall, or other data. In one embodiment, the soil sensor 52 comprises at least one of a soil moisture detector and nutrient level detector. Sensing stations 50 may be deployed in the field, in the geographic area outside of the field, or both.

The data storage may be used to store historical sensor 28 data in the deployed remote sensors 28 until communicated via a wireless transmission or electromagnetic signal by the wireless communications device 56 to at least one of a wireless communications device 20 (e.g., of data processing system 10) and the wireless communications device 26 of the work vehicle electronics 24. The sensing station 50 may transmit the stored sensor 28 data via an electromagnetic signal to a remote data processing system 10 upon interrogation, under a polling scheme, at defined time intervals, upon accumulation of a threshold amount of data, or otherwise. For example, the wireless communications device 26 of the work vehicle electronics may interrogate the sensing station 50 via its wireless communications device 56 which passively listens or receives signals to conserve battery longevity or an electrical charge associated with another energy storage device.

In one configuration, the work vehicle electronics 24 comprises a remote data processing system 10 that is mounted on a work vehicle (e.g., a harvester or a combine) for harvesting the particular crop.

Figure 10:
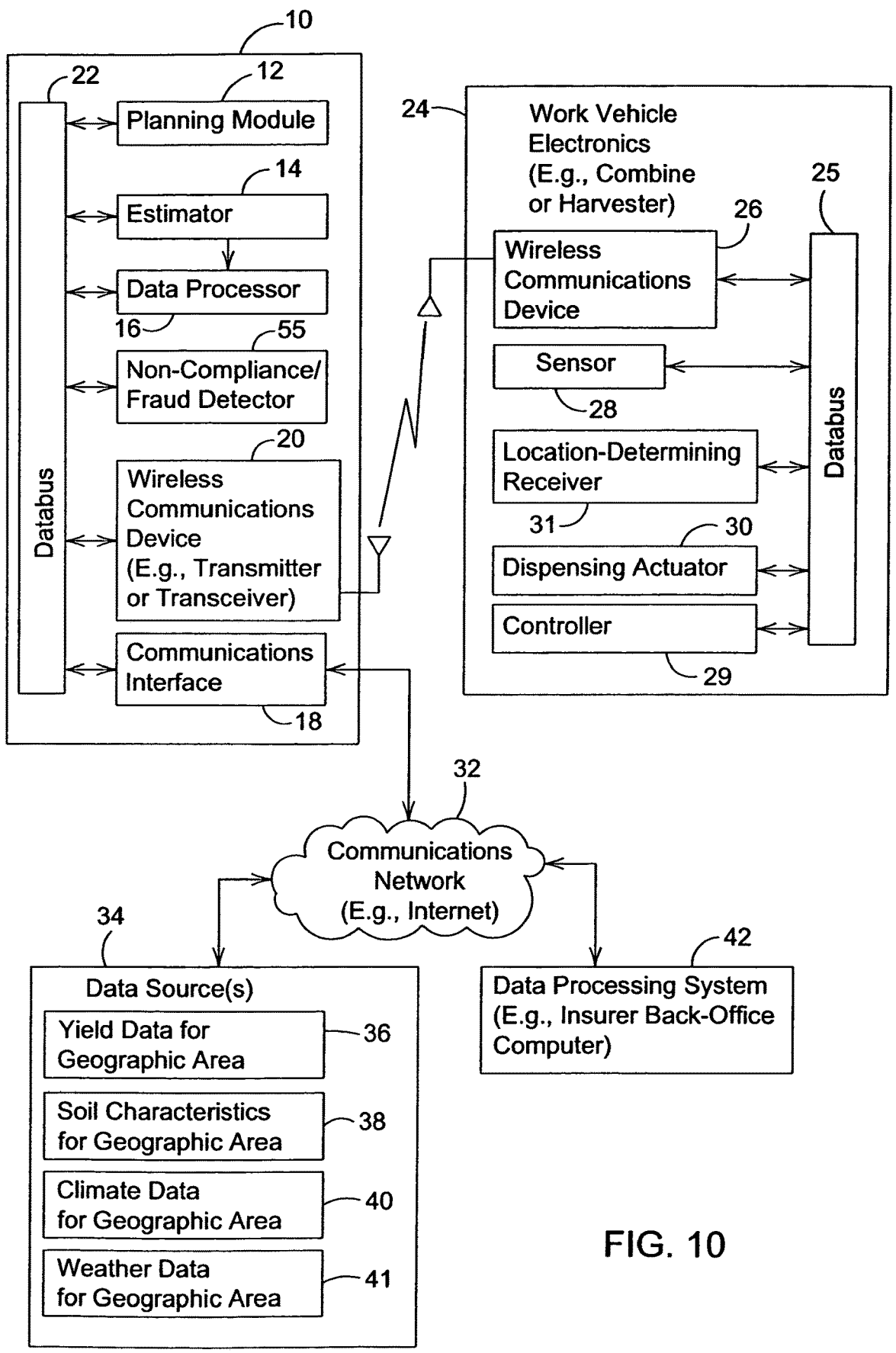
FIG. 10 is a block diagram of still another embodiment of a system for managing a crop insurance program or grower compliance plan.

The system of FIG. 10 is similar to the system of FIG. 1 except the system of FIG. 10 further includes a noncompliance/fraud detector 55 associated with the data processing system 10.

The noncompliance/fraud detector 55 seeks to identify suspicious, fraudulent, or noncompliant activities of the grower, particularly with respect to the growers treatment of the crops and the growers nonconformance with the crop input plan (e.g., Best Management Practices compliant plan) versus the environment contributing to the nonperformance of the crop.

The sensing stations 50 are deployed in the field and in the geographic area outside of the field. Each remote sensing station 50 comprises a weather monitor 54 and a soil sensor (e.g., moisture detector and/or a nutrient level detector) to determine whether any fraudulent manipulation of the field or test strips is taking place. The occurrence of such fraudulent manipulation may be identified by the data processor 16, which may include a non-compliance/fraud detector 55. The non-compliance/fraud detector 55 may comprise a non-compliance detection module that determines whether the grower is intentionally or negligently neglecting the field or providing other crop inputs that are out of the ordinary or not recommended pursuant to the input management plan. The fraudulent incident or potentially fraudulent incident may be reported from the non-compliance/fraud detector 55 or data processor 16 to the data processing system 10 of the insurer. In one embodiment, the sensing station 50 may regularly or periodically detect the moisture level of the soil and the nitrogen level of the soil, if the nitrogen level or the moisture level falls below a minimum reference level, the grower and the insurer may be alerted. The grower may be allotted some maximum time or time window in the contract to correct the nitrogen level by the application of more nitrogen or other fertilizer, crop inputs, or additives. Similarly, the grower may be allotted some maximum time or time window in the contract to correct the moisture level by the application of more water or other additives.

An insurance product comprises a crop risk insurance policy and an endorsement assembly associated with the crop insurance policy. The crop risk insurance policy component may insure against risk of loss for drought or another type of loss, for example. An endorsement assembly is associated with the crop risk insurance policy component. The endorsement assembly comprises a grower compliance requirement requiring a grower to comply with a qualified crop input plan (e.g., Best Management Practices compliant plan) for a particular crop in a field. For instance, right of payment is contingent upon a first yield per unit land area of the particular crop in the field less than second yield per unit land area of a geographic area by more than a threshold amount. The geographic area covers a greater area than the field and representative of at least one of the soil characteristics and the climate associated with the field. Further, the right of payment is generally contingent upon compliance of the grower with the ancillary terms and conditions. In one embodiment, the minimum threshold percentage is approximately five percent.

The geographic area comprises one or more of the following: a country, a state, a county, a province, a canton, a region, a weather growing zone, a rainfall zone, a climate zone, and a soil parameter zone. To provide accurate information for risk management of the insurance policy, premium determination, or both, the first yield per land unit is measured by at least one of a mass sensor 28, a weight sensor 28, flow sensor 28, a moisture sensor 28, a piezoelectric transducer, a grain flow sensor 28, a grain moisture sensor 28, a ground speed sensor 28, a header position switch, an impact force sensor 28, a plate displacement sensor 28, a volume measurement device, a load cell system, a radiometric system, and a capacitance sensor 28. In one configuration, a sensor 28 detects the first yield per land unit at one of a harvester and a combine; and a transmitter associated with the sensor 28 transmits the first yield per land unit to a data processing system 10 via an electromagnetic signal. The electromagnetic signal may be encrypted or transmitted via a spread spectrum signal for security.

The ancillary terms and conditions of the crop insurance policy may require the grower to establish or have established a test strip and at least one check strip associated with the test strip a the field. The ancillary terms and conditions include identifying different zones in the field based on at least one of soil properties and previously grown crops and associating a test strip with each identified different zone. The zones are based on a crop history for the zone, a crop input history for the zone, a historic nutrient exposure of the zone, and a nutrient mobility rating associated with the zone, and a hydraulic mobility rating associated with the zone, and an irrigated zone versus a non-irrigated zone.

With respect certain configurations of BMP or other crop insurance or crop endorsements, a test strip is established in the field. At least one check strip is associated with or adjoins the test strip a the field. With respect to other configurations of BMP or crop insurance or endorsements, multiple test strips are positioned in the field based on soil zones that are most representative of the entire field. A soil survey may be used to identify different zones in the field based on at least one of soil properties and previously grown crops; a test strip being associated with each identified different zone.

Soil surveys may be commercially available, available through university studies, state sponsored studies, the Department of Agriculture, National Resource Conservation service, governmental studies, or studies may be commissioned by growers. Soil surveys may be expressed as maps or data on soil properties or soil types. Growers may complete soil sampling or soil testing regularly or periodically to determine or estimate soil properties or soil types. Soil properties include organic matter content, texture, structure, density, porosity, cation exchange capacity, topography, slope drainage, soil depth, compaction, and pH. A soil type may be defined by different combinations of soil properties, wherein each soil property is associated with a corresponding value range. The cation exchange capacity is a measure of nutrient availability and refers to the total quantity of negatively charged particles in the soil that are available to attract positively charged particles (e.g., cations).

In one embodiment, the zones are based on one or more of the following: a crop history for the zone, a crop input history for the zone, a historic nutrient exposure of the zone, and a nutrient mobility rating associated with the zone, and a hydraulic mobility rating associated with the zone, and an irrigated zone versus a non-irrigated zone. In another embodiment, the zones are based on soil types, soil properties and corresponding values or ranges of values, or all of the foregoing items.

Having described the preferred embodiment, it will become apparent that various modifications can be made without departing from the scope of the invention as defined in the accompanying claims.

We claim:

1. A method for managing a crop insurance program or a grower compliance plan via a first data processing system comprising a data processor coupled to a data bus, the method comprising:

determining an input management plan, by a planning module of the first data processing system, that specifies parameters for application of a crop input to a field having a field area within a geographic area that is greater in geographic scope than the field area, the input management plan comprising a minimum reference nitrogen level;

determining whether the field is compliant with the input management plan by detecting a soil nitrogen level of the field, wherein the field is compliant with the input management plan if the soil nitrogen level of the field is above the minimum reference nitrogen level;

if it is determined that the field is not compliant with the input management plan, sending an alert that the soil nitrogen level of the field is below the minimum reference nitrogen level, wherein the alert comprises instructions for correction of the soil nitrogen level by application of a corrective amount of additional nitrogen fertilizer within an allotted maximum time;

if it is determined that the field is not compliant with the input management plan, applying the corrective amount of additional nitrogen fertilizer to the field to correct the soil nitrogen level to above the minimum reference nitrogen level;

measuring, by a yield sensor on a harvesting work vehicle, a field yield associated with a particular crop while harvesting the particular crop from the field;

determining whether other fields within the geographic area are compliant with the input management plan by detecting a soil nitrogen level of the other fields using remote sensors deployed in the other fields, wherein the remote sensors are in communication with the first data processing system;

estimating, by an estimator of the first data processing system, an aggregate yield of the particular crop associated with the geographic area based on the other fields within the geographic area determined to be compliant fields that comply with the input management plan;

determining, by the first data processing system, a difference between the field yield and the aggregate yield; and making available, by a communications interface of the first data processing system, the determined difference and a field identifier associated with the field to a receiving entity that is associated with at least one of claims and insurance on the field, where the making available comprises transmitting information on the determined difference and field identifier to a second data processing system via a communications network.

2. The method according to claim 1 wherein making available comprises transmitting the difference electronically to an insurer as the receiving entity.

3. The method according to claim 1 wherein the making available comprises transmitting the difference to the receiving entity if the field yield and the aggregate yield differs by more than a minimum threshold percentage.

4. The method according to claim 3 wherein the minimum threshold percentage is approximately five percent.

5. The method according to claim 1 wherein the geographic area comprises one or more of the following: a country, a state, a county, a province, a canton, a region, a weather growing zone, a rainfall zone, a climate zone, and a soil parameter zone, and wherein each soil zone is identified by soil properties associated with the depletion, leaching availability, or unavailability of one or more soil nutrients or water.

6. The method according to claim 1 wherein the measuring of the field yield is measured by the yield sensor comprising at least one of a mass sensor, a weight sensor, flow sensor, a moisture sensor, a piezoelectric transducer, a grain flow sensor, a grain moisture sensor, a ground speed sensor, a header position switch, an impact force sensor, a plate displacement sensor, a volume measurement device, a load cell system, a radiometric system, and a capacitance sensor.

7. The method according to claim 1 wherein the measuring of the field yield comprises detecting a first yield per land unit at the harvesting work vehicle, wherein the harvesting work vehicle is one of a harvester and a combine; and further comprising:

transmitting the first yield per land unit to the first data processing system via an electromagnetic signal.

8. The method according to claim 1 wherein the estimating the aggregate yield excludes the yields associated with compliant fields within the geographic area that follow the input management plan.

9. The method according to claim 1 wherein the estimating the aggregate yield excludes the yields associated with noncompliant fields within the geographic area that do not follow the input management plan.

10. The method according to claim 1 further comprising: deploying remote sensors in the field and in a geographic area outside of the field, wherein each remote sensor comprises at least one of a weather monitor, a soil moisture detector, and a nutrient level detector.

11. The method according to claim 10 further comprising: storing historical sensor data in the deployed remote sensors; communicating the stored sensor data via an electromagnetic signal to the first data processing system upon interrogation.

12. The method according to claim 1 wherein the first data processing system is mounted on the harvesting work vehicle, wherein the harvesting work vehicle is one of a harvester and a combine.

13. The method according to claim 1 further comprising establishing a test strip and at least one check strip associated with the test strip in the field.

14. The method according to claim 13 wherein a sensing station is positioned within the test strip.

15. The method according to claim 1 further comprising: identifying different zones in the field based on at least one of soil properties and previously grown crops; and associating a test strip with each identified different zone.

16. The method according to claim 15 wherein the zones are based on a crop history for the zone, a crop input history for the zone, a historic nutrient exposure of the zone, and a nutrient mobility rating associated with the zone, a hydraulic mobility rating associated with the zone, and an irrigated zone versus a non-irrigated zone.

17. The method according to claim 1 wherein the aggregate yield comprises the aggregate yield scaled with reference to a land area equivalent to that of the field area.

18. The method according to claim 1 further comprising: providing a grower of the particular crop on the field with a zone-based
prescription for the application of a crop input within an allotted time for noncompliant zones within the field; and
notifying the insurer or other party of noncompliance with the zone-based prescription of the grower fails to comply with the zone-based prescription within the allotted time.

19. The method according to claim 1, wherein the yield sensor comprises a moisture detector that is configured to measure moisture content of the particular crop, and further comprising adjusting the field yield to compensate for the moisture content of the particular crop.

20. The method according to claim 1, where the soil nitrogen level, as sensor data, is regularly or periodically detected at corresponding measurement times with time stamps and stored by a sensing station in the field, and wherein the alerting is performed using a-wireless communication of the sensing station.

21. The method according to claim 20 further comprising: communicating the sensor data via wireless transmission from a data storage of the sensing station to the work vehicle electronics of a work vehicle and the first data processing system.

22. A system for managing a crop insurance program or a grower compliance plan, the system comprising:
a planning module, of a first data processing system, that determines an input management plan that specifies parameters for application of a crop input to a target field having a target field area within a defined geographic area that is greater in geographic scope than the target field area, the input management plan comprising a quantity and a concentration of nitrogen fertilizer to be applied to the target field;
a sensing station in the target field that regularly or periodically detects and stores a soil nitrogen level of the target field at corresponding measurement times with time stamps, wherein the sensing station transmits by wireless communication an alert if the soil nitrogen level of the target field is below a minimum reference level, wherein the alert comprises instructions for correction of the soil nitrogen level of the target field by application of an additional crop input within an allotted maximum time;
a work vehicle equipped with work vehicle electronics, wherein the work vehicle is configured to harvest a particular crop from the field such that the work vehicle receives the particular crop from the field in a path of crop flow, wherein the work vehicle electronics comprises:
a work vehicle sensor positioned in the path of crop flow, wherein the work vehicle sensor is configured to measure a field yield of the particular crop in the field while the work vehicle receives the crop in the path of crop flow;
a communications device in communication with the work vehicle sensor through a work vehicle data bus and further in communication with the first data processing system, wherein the communications device is configured to receive the parameters for application of the crop input from the first data processing system; and
a dispensing actuator in communication with the communications device through the work vehicle data bus, wherein the dispensing actuator is configured to apply the crop input to the field according to the parameters received by the communications device;
the first data processing system is configured to determine whether other fields within the geographic area are compliant with the input management plan by detecting a soil nitrogen level of the other fields;
an estimator, of the first data processing system, that estimates an aggregate yield of the particular crop within a geographic zone associated with the defined geographic area based on the other fields within the geographic area determined to be compliant fields that comply with the input management plan;
the first data processing system is further configured to determine a difference or variation between the field yield and the aggregate yield; and
a communications interface, of the first data processing system, that makes available the determined difference and a field identifier associated with the field to a receiving entity that is associated with at least one of claims and insurance on the field, where the making available comprises transmitting information to a second data processing system via a communications network.

23. The system according to claim 22 wherein the communications interface comprises a transmitter for transmitting the difference electronically to an insurer as the receiving entity.

24. The system according to claim 22 wherein the communications interface comprises a transmitter for transmitting the difference to the receiving entity if the field yield and the aggregate yield differs by more than a minimum threshold percentage.

25. The system according to claim 24 wherein the minimum threshold percentage is approximately five percent.

26. The system according to claim 22 wherein the geographic area comprises one or more of the following: a country, a state, a county, a province, a canton, a region, a weather growing zone, a rainfall zone, a climate zone, and a soil parameter zone, and wherein each soil zone is identified by soil properties associated with the depletion, leaching availability, or unavailability of one or more soil nutrients or water.

27. The system according to claim 22 wherein the yield sensor comprises at least one of a mass sensor, a weight sensor, flow sensor, a moisture sensor, a piezoelectric transducer, a grain flow sensor, a grain moisture sensor, a ground speed sensor, a header position switch, an impact force sensor, a plate displacement sensor, a volume measurement device, a load cell system, a radiometric system, and a capacitance sensor.

28. The system according to claim 22 wherein the aggregate yield comprises the aggregate yield scaled with reference to a land area equivalent to that of the field area.

29. The system according to claim 22 further comprising: a data storage device of the sensing station for storing sensor data until
communicated via wireless transmission from the data storage of the sensing station to the work vehicle electronics of a work vehicle and the first data processing system.

30. A method for managing the characteristics of a crop in a target field, the method comprising the steps of:
a. deploying at least one work vehicle into the target field, wherein the target field comprises a field area within a geographic area that is greater in geographic scope than the field area of the target field, wherein the at least one work vehicle is one of a harvester and a combine, and wherein the at least one work vehicle comprises;
i. a work vehicle sensor; and
ii. a communications device;
b. positioning at least one sensor in the target field, wherein the at least one sensor of the target field is in communication with the communications device of the at least one work vehicle;
c. applying a crop input management plan to the target field to obtain a target field characteristic associated with the target field in compliance with a criteria characteristic, wherein applying the crop input management plan comprises:
i. applying via the at least one work vehicle a crop input to the target field;
ii. recording via the at least one sensor of the target field the target field characteristic associated with the target field;
iii. determining whether the target field characteristic recorded via the at least one sensor of the target field is compliant with the criteria characteristic;
iv. if the target field characteristic recorded via the at least one sensor of the target field is not compliant with the criteria characteristic, transmitting to the communications device of the at least one work vehicle a prescription for correcting the target field characteristic, wherein the prescription comprises an additional amount of a crop input necessary to correct the target field characteristic; and
v. if the target field characteristic recorded via the at least one sensor of the target field is not compliant with the criteria characteristic, applying via the at least one work vehicle the additional amount of crop input necessary to correct the target field characteristic;
d. after applying the crop input management plan to the target field, harvesting the crop in the target field using the at least one work vehicle such that the crop is received by the at least one work vehicle in a path of crop flow;
e. determining a target field yield associated with the crop of the target field, wherein the determining of the target field yield comprises measuring a quantity of the crop harvested by the at least one work vehicle via the work vehicle sensor, wherein the work vehicle sensor is positioned in the path of crop flow;
f. recording via a plurality of reference field sensors located in a plurality of reference fields within the geographic area a reference field characteristic for each of the plurality of reference fields;
g. determining whether the reference field characteristic of each of the plurality of reference fields is compliant with the criteria characteristic;
h. estimating an aggregate yield of the crop associated with the geographic area based on the reference fields in the geographic area having reference field characteristics determined to be compliant with the criteria characteristic;
i. determining a difference between the target field yield and the aggregate yield; and
j. communicating to a receiving entity via the communications device of the at least one work vehicle the determined difference and a field identifier associated with the target field.

* * * * *